United States Patent
Newman, Jr.

(10) Patent No.: US 9,427,504 B2
(45) Date of Patent: Aug. 30, 2016

(54) MEDICAL APPARATUS FOR SUCTION AND COMBINATION IRRIGATION AND SUCTION

(75) Inventor: Lionel Newman, Jr., Los Angeles, CA (US)

(73) Assignee: Wet Nose Technologies, LLC, Los Angeles, CA (US)

(*) Notice: Subject to any disclaimer, the term of this patent is extended or adjusted under 35 U.S.C. 154(b) by 383 days.

(21) Appl. No.: 11/849,268

(22) Filed: Sep. 1, 2007

(65) Prior Publication Data

US 2009/0062751 A1 Mar. 5, 2009

(51) Int. Cl.
*A61M 1/00* (2006.01)

(52) U.S. Cl.
CPC .......... *A61M 1/0039* (2013.01); *A61M 1/0047* (2013.01)

(58) Field of Classification Search
CPC ......... A61M 1/0064; A61M 16/0666; A61M 1/0058; A61M 16/0463; A61M 3/02; A61M 3/0225; A61M 1/0039; A61M 1/0047; A61F 9/008
USPC ............. 604/19, 27, 30, 35, 37, 43, 75, 118, 604/119, 133, 246, 540, 36, 45
See application file for complete search history.

(56) References Cited

U.S. PATENT DOCUMENTS

| | | | |
|---|---|---|---|
| 1,304,327 A | 5/1919 | Klay | |
| 1,314,855 A | 9/1919 | Carpenter | |
| 1,889,425 A * | 11/1932 | Sorensen | 604/35 |
| 2,088,720 A | 8/1937 | Poliniak | |
| 2,295,528 A | 9/1942 | Cutter et al. | |
| 2,328,995 A | 9/1943 | Olds | |
| 2,375,711 A | 5/1945 | Vondrak | |
| 2,422,702 A | 6/1947 | Rodanet | |
| 2,449,497 A | 9/1948 | McLeod | |
| 2,812,765 A | 11/1957 | Tofflemire | |

(Continued)

FOREIGN PATENT DOCUMENTS

| EP | 0979660 A | 2/2000 |
|---|---|---|
| EP | 1084727 | 4/2006 |

(Continued)

OTHER PUBLICATIONS

PCT International Search Report, Nov. 6, 2008.

(Continued)

*Primary Examiner* — Emily Schmidt
*Assistant Examiner* — Lauren M Peng
(74) *Attorney, Agent, or Firm* — Amin, Turocy & Watson, LLP

(57) ABSTRACT

A finger-controlled combination irrigation and suction device is provided. The device includes a handpiece. The handpiece includes: a shaft having a first end and a second end, and having a channel disposed from the first end of the shaft to the second end of the shaft for allowing suction through the shaft; a nozzle coupled to the first end of the shaft; an inlet disposed through an exterior surface of the shaft and in operable communication with the channel, the inlet being disposed to be manually covered and uncovered by one or more fingers of a single hand of a primary caregiver for control of suction through the shaft; and a conduit having a first end disposed to receive a volume of irrigation solution after one or more fingers of the single hand of the primary caregiver act upon an irrigation source proximate to the conduit.

12 Claims, 9 Drawing Sheets

(56) References Cited

U.S. PATENT DOCUMENTS

| | | | |
|---|---|---|---|
| 3,065,749 A | 11/1962 | Brass | |
| 3,710,780 A | 1/1973 | Milch | |
| 3,749,090 A * | 7/1973 | Stewart | A61M 1/0064 604/33 |
| 3,804,089 A * | 4/1974 | Bridgman | 604/43 |
| 3,827,433 A | 8/1974 | Shannon | |
| 3,949,749 A | 4/1976 | Stewart | |
| 3,972,326 A | 8/1976 | Brawn | |
| 4,080,989 A | 3/1978 | Chapelsky et al. | |
| 4,215,476 A | 8/1980 | Armstrong | |
| 4,299,221 A * | 11/1981 | Phillips et al. | 604/30 |
| 4,459,983 A | 7/1984 | Beyreuther et al. | |
| 4,464,316 A | 8/1984 | Michaels | |
| 4,468,216 A * | 8/1984 | Muto | 604/43 |
| 4,617,013 A * | 10/1986 | Betz | A61M 1/0064 600/249 |
| 4,634,420 A | 1/1987 | Spinosa et al. | |
| 4,857,047 A | 8/1989 | Amoils | |
| 5,167,622 A * | 12/1992 | Muto | 604/35 |
| 5,255,675 A | 10/1993 | Kolobow | |
| 5,263,934 A | 11/1993 | Haak | |
| 5,269,296 A | 12/1993 | Landis | |
| D358,475 S | 5/1995 | Choksi et al. | |
| 5,477,852 A | 12/1995 | Landis et al. | |
| 5,557,049 A | 9/1996 | Ratner | |
| 5,575,774 A | 11/1996 | Chen | |
| 5,626,565 A | 5/1997 | Landis et al. | |
| 5,653,231 A * | 8/1997 | Bell | 128/207.16 |
| 5,687,715 A | 11/1997 | Landis et al. | |
| 5,730,727 A * | 3/1998 | Russo | A61M 1/0047 137/517 |
| 5,792,098 A * | 8/1998 | Felix | A61M 1/0084 604/27 |
| D410,021 S | 5/1999 | Heyman et al. | |
| 5,899,878 A | 5/1999 | Glassman | |
| 6,041,777 A | 3/2000 | Faithfull et al. | |
| 6,045,516 A * | 4/2000 | Phelan | 600/579 |
| 6,050,263 A | 4/2000 | Choksi et al. | |
| 6,149,622 A | 11/2000 | Marie | |
| D439,973 S | 4/2001 | Choksi | |
| D449,378 S | 10/2001 | Rogone et al. | |
| 6,494,203 B1 | 12/2002 | Palmer | |
| 6,520,021 B1 | 2/2003 | Wixey et al. | |
| D474,269 S | 5/2003 | Choksi et al. | |
| 6,576,191 B1 | 6/2003 | Myrick et al. | |
| 6,770,050 B2 | 8/2004 | Epstein | |
| 6,795,722 B2 | 9/2004 | Sheraton et al. | |
| 6,805,120 B1 | 10/2004 | Jeffrey et al. | |
| 6,805,129 B1 | 10/2004 | Pless et al. | |
| D506,547 S | 6/2005 | Cruz et al. | |
| 6,958,050 B1 | 10/2005 | Choski et al. | |
| 7,066,917 B2 | 6/2006 | Talamonti | |
| 7,077,154 B2 | 7/2006 | Jacobs et al. | |
| 7,185,681 B2 * | 3/2007 | Romano | 141/9 |
| D590,056 S | 4/2009 | McCrary et al. | |
| 7,601,001 B1 | 10/2009 | McCrary et al. | |
| 2001/0044599 A1 | 11/2001 | Lo | |
| 2002/0108614 A1 * | 8/2002 | Schultz | A61B 19/42 128/207.14 |
| 2003/0047185 A1 | 3/2003 | Olsen et al. | |
| 2003/0065263 A1 | 4/2003 | Hare et al. | |
| 2003/0069553 A1 | 4/2003 | Talamonti | |
| 2003/0132249 A1 * | 7/2003 | Romano | A61J 1/05 222/181.1 |
| 2004/0065330 A1 | 4/2004 | Landis | |
| 2004/0244804 A1 | 12/2004 | Olsen et al. | |
| 2005/0049547 A1 * | 3/2005 | Anspach | A61M 1/0058 604/27 |
| 2005/0072470 A1 | 4/2005 | Jacobs et al. | |
| 2005/0150505 A1 | 7/2005 | Burrow et al. | |
| 2005/0182353 A1 | 8/2005 | Schmidberger et al. | |
| 2005/0256462 A1 | 11/2005 | Underwood | |
| 2005/0277898 A1 | 12/2005 | Dimalanta et al. | |
| 2006/0079832 A1 | 4/2006 | Akahoshi | |
| 2006/0229632 A1 | 10/2006 | Madden et al. | |
| 2007/0078378 A1 | 4/2007 | Kao et al. | |
| 2007/0107737 A1 | 5/2007 | Landis et al. | |
| 2007/0175473 A1 | 8/2007 | Lewis et al. | |
| 2007/0191783 A1 | 8/2007 | Shaw et al. | |
| 2009/0062751 A1 * | 3/2009 | Newman, Jr. | A61M 1/0039 604/246 |

FOREIGN PATENT DOCUMENTS

| | | |
|---|---|---|
| WO | 98/58694 A | 12/1998 |
| WO | 01/64272 A | 9/2001 |
| WO | 2004/033007 A1 | 4/2004 |

OTHER PUBLICATIONS

PCT Written Opinion of the International Searching Authority.
International Search Report mailed Nov. 6, 2008 for International Application No. PCT/US2008/074748, 2 pages.
International Search Report mailed Nov. 6, 2008 for International Application No. PCT/US2008/074574, 2 pages.
International Search Report mailed Nov. 2, 2004 for International Application No. PCT/IB2003/04419, 2 pages.
Fisher & Paykel Healthcare Product Catalog copyright 2004, 16 pages.
Fisher & Paykel Healthcare Annual Report 2002, 32 pages.
Petry, Fisher & Paykel 510(k) Summary of Safety and Effectiveness Information, 6 pages, Apr. 3, 2003.
http://www.fphcare.com/rsc.html, last accessed Apr. 26, 2010, 1 page.
http://www.fphcare.com/rsc/infant-care/resuscitation.html, last accessed Apr. 26, 2010, 1 page.
http://www.fphcare.com/rsc/infant-care/non-invasive-ventilation.html, last accessed Apr. 26, 2010, 1 page.
http://www.fphcare.com/rsc/rac-clinical-and-applications/infant-c-a/why-bubble-cpap-is-vital.html, last accessed Apr. 26, 2010, 2 pages.
http://www.fphcare.com/product-overview/chambers/humidification-chambers/mr290-autofeed.html, last accessed Apr. 26, 2010, 1 page.
http://www.fphcare.com/product-overview/chambers/humidification-chambers/mr210-mr250-chamber.html, last accessed Apr. 26, 2010, 1 page.
http://www.fphcare.com/product-overview/chambers/humidification-chambers/mr225-manual-feed.html, last accessed Apr. 26, 2010, 1 page.
http://www.fphcare.com/osa/cpap-solutions/cpap/sleepstyle-200.html, last accessed Apr. 26, 2010, 2 pages.
http://www.fphcare.com/osa/cpap-solutions/cpap/sleepstyle-240.html, last accessed Apr. 26, 2010, 2 pages.
http://www.fphcare.com/osa/cpap-solutions/cpap/sleepstyle-600.html, last accessed Apr. 26, 2010, 2 pages.
http://www.fphcare.com/osa/cpap-solutions/autocpap/sleepstyle-250.html, last accessed Apr. 26, 2010, 2 pages.
Babi.Plus™ Bubble PAP Valve 0—10 cm H20, Safe, accurate method to deliver CPAP therapy in neonatal critical care environments, 2010, 1 page.
B&B Medical Technologies, Babi.Plus™ Bubble PAP Valve 0—10 cm H2O, 2005, 2 pages.
B&B Medical Technologies, Babi.Plus™ Bubble PAP Valve 0—10 cm H2O gives clinicians a safe, accurate, convenient method to deliver CPAP therapy for neonates and premature infants, 1 page, Mar. 19, 2010.
Airways Development LLC, Waterseal Canister & Accessories, Aug. 2004, 1 page.
A Plus Medical 510(k) Summary, 5 pages, May 20, 2009.
Presentation Jul. 2007, 16 pages.
http://www.airwaysdevelopment.com/product.asp, last accessed Apr. 28, 2010, 1 page.
Frischer, et al. Eosinophil-derived proteins in nasal lavage fluid of neonates of allergic parents and the development of respiratory symptoms during the first 6 months of life. Allergy 2000: 55: 773-777, ISSN 0105-4538. http://onlinelibrary.wiley.com/doi/10.1034/j.1398-9995.2000.00773.x/pdf. Last accessed Oct. 6, 2010, 5 pages.

(56) References Cited

OTHER PUBLICATIONS

Waisman. Non-Traumatic Nasopharyngeal Suction in Premature Newborn Infants with Upper Airway Obstruction from Secretions Following Nasal CPAP. J Pediatr 2006;149:279. http://download.journals.elsevierhealth.com/pdfs/journals/0022-3476/PIIS002234760600148X.pdf. Last accessed Oct. 6, 2010, 1 page.
Okada, et al. Pressure-Controlled Dual Irrigation-Suction System for Microneurosurgery: Technical Note. www.neurosurgery-online.com, E625, vol. 65, No. 3, Sep. 2009. http://pt.wkhealth.com/pt/re/merck/dpdfhandler.00006123-200909000-00032.pdf; jsessionid=MsvLyq9Y7c928drTcGsSkYzDJy61CfX4zbyC66q6kcxL5Ghd-RLKy!1137524313!181195628!8091!-1. Last accessed Oct. 6, 2010, 4 pages.
Vain, et al. Oropharyngeal and nasopharyngeal suctioning of meconium-stained neonates before delivery of their shoulders: multicenter, randomized controlled trial (Abstract), The American College of Obstetricians and Gynecologists, vol. 104, No. 5, Part 1, Nov. 2004.
Garzon, et al. Management of Respiratory Syncytial Virus With Lower Respiratory Tract Infection in Infants and Children. AACN Clinical Issues, vol. 13, No. 3, Aug. 2002, pp. 421-430.
Balfour-Lynn, et al. Nasal IgA response in wheezy infants. Archives of Disease in Childhood 1993; 68: 472-476. Last accessed Oct. 18, 2010, 5 pages.
Celik, et al. A Current Conflict: Use of Isotonic Sodium Chloride Solution on Endotracheal Suctioning in Critically Ill Patients. Dimens Crit Care Nurs. 2006;25(1):11/14. http://www.nursingcenter.com/pdf.asp?AID=630764. Last accessed Oct. 18, 2010, 4 pages.
Stokowski (Section Editor). Endotracheal Suctioning Increases Cerebral Blood Flow in the Very Low Birth-Weight Infant, Advances in Neonatal Care: Apr. 2008—vol. 8—Issue 2—pp. 75-77. doi: 10.1097/01. ANC.0000317254.30460.5d, Noteworthy Professional News, downloaded Mar. 24, 2008, 3 pages.
Virolainen, et al. New Method to Assess Dilution of Secretions for Immunological and Microbiological Assays. Journal of Clinical Microbiology, May 1993, p. 1382-1384, vol. 31, No. 5. http://jcm.asm.org/cgi/reprint/31/5/1382. Last accessed Oct. 19, 2010, 3 pages.
Heikkinen, et al. Quantification of Cytokines and Inflammatory Mediators in Samples of Nasopharyngeal Secretions with Unknown Dilution. Pediatric Research: Feb. 1999—vol. 45—Issue 2—pp. 230-234. http://journals.lww.com/pedresearch/Fulltext/1999/02000/Quantification_of_Cytokines_and_Inflammatory.12.aspx#. Last accessed Oct. 19, 2010, 9 pages.
Foglia, et al. Ventilator-Associated Pneumonia in Neonatal and Pediatric Intensive Care Unit Patients. Clinical Microbiology Reviews, vol. 20, No. 3, Jul. 2007, p. 409-425. http://cmr.asm.org/cgi/reprint/20/3/409.pdf. Last accessed Oct. 19, 2010, 17 pages.
Kaiser, et al. Tracheal suctioning is associated with prolonged disturbances of cerebral hemodynamics in very low birth weight infants. Journal of Perinatology (2008) 28, 34-41, published online, Oct. 25, 2007. http://www.umanitoba.ca/faculties/medicine/units/pediatrics/sections/neonatology/media/Oct20-08.pdf. Last accessed Oct. 19, 2010, 8 pages.
Folk. Guide to Capillary Heelstick Blood Sampling in Infants. Advances in Neonatal Care • vol. 7, No. 4 • pp. 171-178. http://www.nursingcenter.com/pdf.asp?AID=735611. Last accessed Oct. 19, 2010, 8 pages.
Lasocki, et al. Open and Closed-circuit Endotracheal Suctioning in Acute Lung Injury: Efficiency and Effects on Gas Exchange. Anesthesiology: Jan. 2006—vol. 104—Issue 1—pp. 39-47, Clinical Investigations. http://journals.lww.com/anesthesiology/Fulltext/2006/01000/Open_and_Closed_circuit_Endotracheal_Suctioning_in.8.aspx. Last accessed Oct. 19, 2010, 9 pages.
Lanter. Clinical Research and the Development of New Devices: Considerations for Nurses. Dimensions of Critical Care Nursing: May/Jun. 2007—vol. 26—Issue 3—pp. 117-120. http://journals.lww.com/dccnjournal/Fulltext/2007/05000/Clinical_Research_and_the_Development_of_New.7.aspx. Last accessed Oct. 19, 2010, 4 pages.
National Nosocomial Infections Surveillance (NNIS) System Report, data summary from Jan. 1992 through Jun. 2004, issued Oct. 2004. http://www.cdc.gov/ncidod/dhqp/pdf/nnis/2004NNISreport.pdf. Last accessed Oct. 19, 2010, 16 pages.
Ingram, et al. Eosinophil Cationic Protein in Serum and Nasal Washes from Wheezing Infants and Children. Journal of Pediatrics, vol. 127, issue 4, Oct. 1995. Retrieved from the internet on Nov. 10, 2010, 11 pages.
Heikkenen, et al. Free Secretory Component as a Standardization Protein for Nasopharyngeal Specimens from Children with Upper Upper Respiratory Tract Infection. Acta Paediatr 88: 150-153, 1999.
Bonner, et al. The Nursing Care of the Infant Receiving Bubble CPAP Therapy. Advances in Neonatal Care • vol. 8, No. 2 • pp. 78-95. Last accessed Nov. 13, 2010, 18 pages.
Klimek, et al. Norm Values for Eosinophil Cationic Protein in Nasal Secretions: Influence of Specimen Collection. Clinical and Experimental Allergy, 1999, vol. 29, pp. 367-374.
Norris, et al. Nursing Procedures and Alterations in Transcutaneous Oxygen Tension in Premature Infants. Nursing Research, vol. 31, No. 6, Nov./Dec. 1982, pp. 330-336.
Samolinski, et al. Changes in Nasal Cavity Dimensions in Children and Adults by Gender and Age. Laryngoscope, 117:1429-1433, Aug. 2007, The American Laryngological, Rhinological and Otological Society, Inc.
Weinstein, et al. Recommendations of the Panel on Cost-Effectiveness in Health and Medicine. JAMA, Oct. 16, 1996—vol. 276, No. 15, 6 pages.

* cited by examiner

MEDICAL APPARATUS FOR SUCTION AND COMBINATION IRRIGATION AND SUCTION

FIELD OF THE INVENTION

The present invention relates to medical devices and, in particular, to medical devices providing irrigation and suction.

BACKGROUND

Living beings such as humans and animals produce fluids as part of normal bodily functions. In some cases, the fluids are secretions from the nose or the mouth. In other cases, the fluids are accumulations of secretions that may change form over time, such as ear wax. Oftentimes, removal of the fluids is medically necessary or preferred. For example, fluids may be removed from the upper airway (i.e., the nose and/or mouth) of a baby, child or adult to aid in respiratory functionality. In another example, fluid such as blood may be removed from a body cavity prior to a medical procedure. In another example, ear wax or other fluid may be removed to aid in auditory functionality.

Manual or automated suction devices are conventionally used to remove fluids. Because the suction device must be placed in close proximity to or inside of the body cavity during suction, injury and trauma to the body and/or body cavity often results due to the design of the nozzle 40 portion of the suction device. Accordingly, there is a need for a suction device designed such that the likelihood of injury to the body and/or body cavity during use is relatively low.

Further, the fluid to be removed from the body cavity may be of a consistency making suction uncomfortable for the patient on which suction is performed. To make the fluid thinner and suction more comfortable, conventional approaches include irrigating the body cavity by depositing solution in the body cavity and then suctioning the fluid and the solution from the body cavity. This process, however, is quite cumbersome as the primary caregiver, whom may be holding or restraining a baby or other patient with one arm and hand, must with the other hand, retrieve an irrigation source, irrigate the body cavity, replace the irrigation source to its original position, retrieve the suction device, suction the body cavity and replace the suction device to its original position. The process may alternately disadvantageously require the assistance of a secondary caregiver to provide the irrigation to and suction of the body cavity while the primary caregiver holds or restrains the patient. The process is, in either case, unnecessarily time-consuming, which may be detrimental to the patient, especially in life-threatening medical emergencies. Accordingly, there is a need for a combination irrigation and suction device that may be operated by a single hand of a primary caregiver such that the primary caregiver may operate the device to perform irrigation and suction with one hand and may perform other medical duties such as holding or restraining a patient with another hand.

SUMMARY OF EMBODIMENTS OF THE INVENTION

One or more embodiments of the present invention include a finger-controlled handpiece for combined irrigation and suction. The handpiece includes: a shaft having a first end and a second end distal from the first end. The shaft also has a channel disposed from the first end of the shaft to the second end of the shaft for allowing suction through the shaft. The handpiece also includes a nozzle coupled to the first end of the shaft; and an inlet disposed through an exterior surface of the shaft and in operable communication with the channel, the inlet being disposed to be manually covered and uncovered by one or more fingers of a single hand of a primary caregiver for control of suction through the shaft. The handpiece also includes a conduit having a first end disposed to receive a volume of irrigation solution after one or more fingers of the single hand of the primary caregiver act upon an irrigation source proximate to the conduit.

In some embodiments, the conduit is coupled to the exterior surface of the nozzle. In some embodiments, the first end of the conduit is coupled to the exterior surface of the shaft in communication with the channel. In some embodiments, the nozzle includes pliable material. In some embodiments, the shaft includes a rigid material.

One or more embodiments of the present invention is a medical kit. The medical kit includes a medical glove wearable by a primary caregiver. The medical kit also includes a finger-controlled handpiece for combined irrigation and suction. The handpiece is disposed with an inlet disposed to be covered and uncovered by one or more fingers of a gloved single hand of a primary caregiver to control suction through the handpiece and a conduit disposed to receive irrigation solution upon one or more fingers of the gloved single hand of the primary caregiver acting upon an irrigation source proximate to the conduit. The kit also includes a receptacle coupleable to the handpiece and being disposed to receive and retain fluid suctioned through the handpiece.

In some embodiments, the kit also includes an irrigation source coupleable to the conduit.

One or more embodiments of the present invention include a finger-controlled system for combined irrigation and suction. The system includes a handpiece and an irrigation source. The handpiece includes a shaft having a first end and a second end distal from the first end, the shaft also having a channel disposed from the first end of the shaft to the second end of the shaft for allowing suction through the shaft. The handpiece also includes a nozzle coupled to the first end of the shaft; and an inlet disposed through an exterior surface of the shaft and in operable communication with the channel. The inlet is disposed to be manually covered and uncovered by one or more fingers of a single hand of a primary caregiver for control of suction through the shaft. The handpiece also includes a conduit having a first end disposed to receive a volume of irrigation solution after one or more fingers of the single hand of the primary caregiver act upon an irrigation source proximate to the conduit; and the irrigation source coupled to the first end of the conduit.

In some embodiments, the irrigation source is an ampule. In some embodiments, the irrigation source is depressable by one or more fingers of the single hand of the primary caregiver. In some embodiments, the system also includes a receptacle coupled to the second end of the shaft and being disposed to receive and retain fluid suctioned through the shaft. In some embodiments, the system also includes a suction mechanism coupled to the second end of the shaft and being disposed to provide suction force through the shaft.

One or more embodiments of the present invention is a finger-controlled handpiece for suctioning a body cavity. The handpiece includes: a shaft having a first end and a second end distal from the first end, the shaft also having a channel disposed from the first end of the shaft to the second end of the shaft for allowing suction through the shaft. The handpiece also includes a nozzle coupled to the first end of the shaft, the nozzle being pliable; and an inlet disposed through an exterior surface of the shaft and in operable communication with the channel, the inlet being disposed to be manually covered and uncovered by one or more fingers of a single hand of a primary caregiver for control of suction through the shaft.

In some embodiments, the nozzle is comprised of rubber. In some embodiments, the nozzle includes an end portion having a substantially flat configuration.

BRIEF DESCRIPTION OF THE DRAWINGS

FIG. 6 is a side view of a finger-controlled handpiece according to an embodiment of the invention.

FIG. 7 is a top view of a finger-controlled handpiece according to an embodiment of the invention.

FIG. 8 is a bottom view of a finger-controlled handpiece according to an embodiment of the invention.

FIG. 9 is a side view of a finger-controlled handpiece according to another embodiment of the invention.

FIG. 10 is a bottom view of a finger-controlled handpiece according to another embodiment of the invention.

FIG. 11 is a side view of a finger-controlled handpiece according to another embodiment of the invention.

FIG. 12 is a top view of a finger-controlled handpiece according to another embodiment of the invention.

FIG. 13 is a side view of a finger-controlled handpiece according to another embodiment of the invention.

DETAILED DESCRIPTION OF EMBODIMENTS OF THE INVENTION

Figure 1:
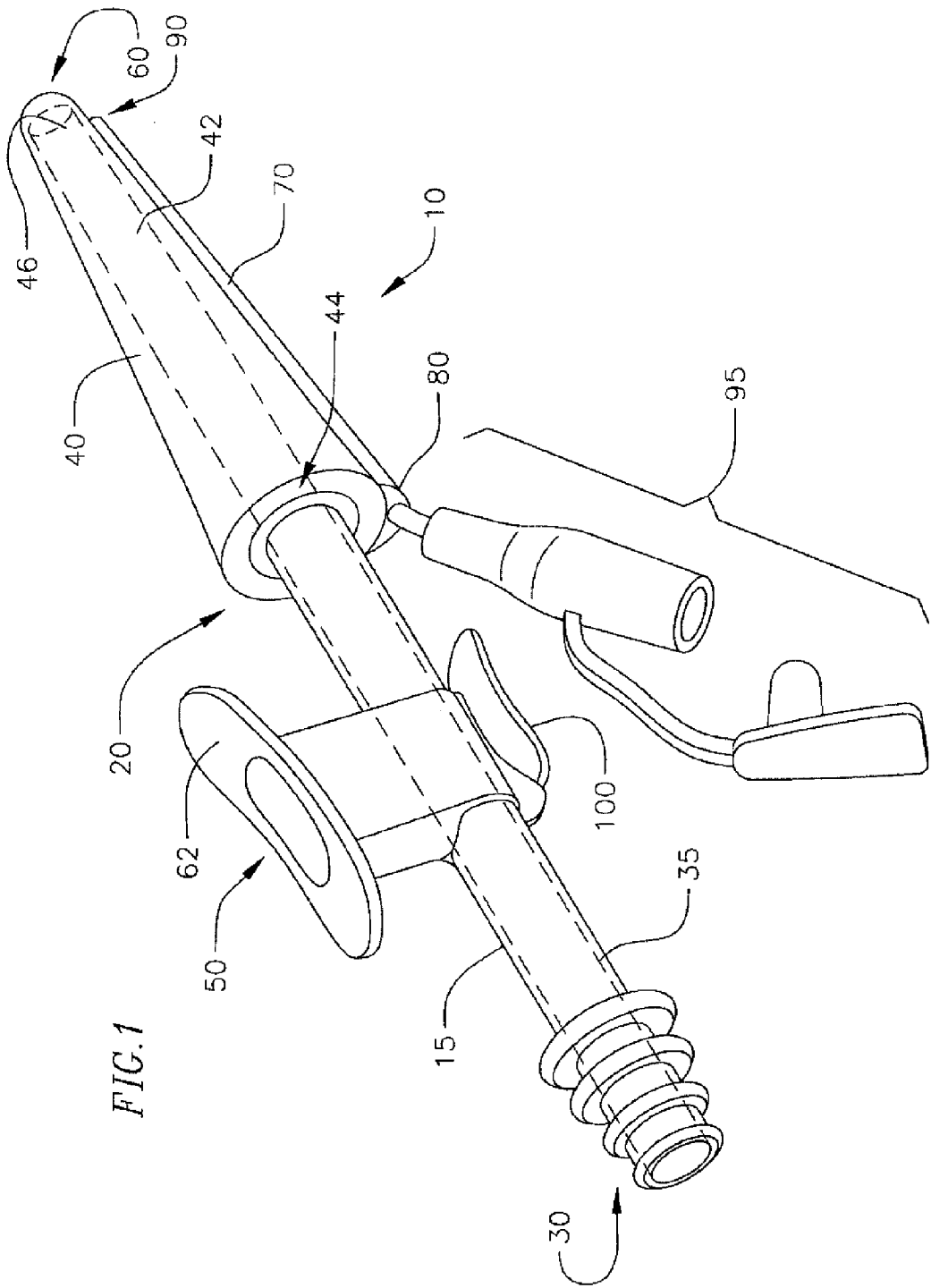
FIG. 1 is a perspective view of a finger-controlled combination irrigation and suction device of a finger-controlled system according to one embodiment of the present invention.

FIG. 1 is a perspective view of a finger-controlled combination irrigation and suction device of a finger-controlled system according to one embodiment of the present invention. The device includes a handpiece 10. The handpiece 10 is a portable device disposed to provide irrigation to a body cavity and to suction the body cavity. The handpiece 10 is disposed to be held and easily manipulated in the hand of a primary caregiver. The handpiece 10 may be held in a first hand of the primary caregiver while the primary caregiver holds or restrains a patient with a second hand of the primary caregiver.

The handpiece 10 includes a shaft 15, a nozzle 40, an inlet 50 and a conduit 70. The shaft 15 includes a first end 20 and a second end 30 distal from the first end 20. The shaft 15 also includes a channel 35 disposed from the first end 20 of the shaft 15 to the second end 30 of the shaft 15 for allowing suction force through the shaft 15 between the first end 20 of the shaft 15 and the second end 30 of the shaft 15. In various embodiments, the first end 20 and/or the second end 30 may have a smooth or ribbed exterior surface facilitating attachment of one or more other components or devices to the shaft 15.

The shaft 15 may be composed of a rigid material, including but not limited to, hardened plastic or glass. Although the embodiment of the handpiece 10 shown illustrates the shaft 15 as elongated and tubular, other designs are possible and are envisaged within the scope of this patent application. In one or more embodiments, the shaft 15 may be any number of shapes that may be held in a single hand of a single caregiver and finger-controlled, including, but not limited to, cube- or dome-shaped.

The handpiece 10 also includes a nozzle 40 coupled to the first end 20 of the shaft 15. The nozzle 40 may be permanently or temporarily coupled to the first end 20 of the shaft 15 through any number of suitable methods. In various embodiments, the nozzle 40 may be welded, joined with adhesive or telescopically coupled to the shaft 15. Additionally, the nozzle 40 may include ridges on the interior of its surface for coupling to ridges of shaft 15.

The nozzle 40 is pliable. In various embodiments, the nozzle 40 is composed substantially of rubber, soft plastic or other pliable material. The nozzle 40 is generally conical-shaped. In various embodiments, the conical-shape may be more slender or less slender. The nozzles may be any of a number of sizes, including those suitable for premature or very low birth-weight babies (e.g., less than 3 pounds), normal birth weight and age or for normal sized babies (e.g., greater than 6-7 pounds). Accordingly, an angle from an end portion 60 of the nozzle 40 to a point on the exterior surface of the nozzle 40 may vary depending on the design of the nozzle 40 and all such variations are envisaged. The nozzle 40 may be coupled to the shaft by any suitable methods, including, but not limited to, welding, screw-on attachment or telescopic attachment.

A channel 42 of the nozzle 40 is located through the nozzle 40 wherein the first end 44 of the channel 42 of the nozzle 40 is in communication with the channel 35 of the shaft 15 and the second end 46 of the channel of the nozzle 40 is positioned near the end portion 60 of the nozzle 40 thereby creating a path for flow of suction force from the second end of the shaft 15 to the end portion of the nozzle 40.

The end portion 60 includes an end portion inlet (not shown) through the end portion 60 from the channel 42 to the outside environment. The end portion inlet in the end portion 60 of the nozzle 40 may be any number of diameters that can provide adequate suction and allow fluids of thick consistency, such as meconium secretions, to travel through the nozzle 40 and into the channel 35 of the shaft 15. Accordingly, when the end portion of the nozzle 40 is provided in close proximity to a body cavity, suction force may be provided to the body cavity through the end portion 60 of the nozzle 40.

The diameter of the end portion 60 and/or the exterior of the nozzle 40 generally may be any number of diameters. Accordingly, a nozzle 40 may be selected according to its design wherein the caregiver may take into account the age and/or medical condition of the patient.

In various embodiments, the end portion 60 may be of any design such that the end portion may meet with a body or body cavity and the likelihood of injury is relatively low. In various embodiments, the end portion 60 is substantially round or substantially flat in configuration. The substantially round and substantially flat configurations may be designed with curvature of various degrees such that one end portion 60 may be designed to be more circular or more angular than other configurations. Similarly, the flat configuration may be somewhat convex, concave or otherwise.

The handpiece 10 also includes an inlet 50 in the exterior surface of the shaft 15. The inlet 50 is in operable communication with the channel 35 of the shaft 15. The inlet 50 is shown located approximately midway between the first end 20 and the second end 30 of the shaft 15 but may be located at any position along the shaft 15 allowing a primary caregiver to cover the inlet 50 with one or more fingers of the single hand of the primary caregiver. The inlet 50 is disposed to be manually covered and uncovered by one or more fingers of a single hand of a primary caregiver for control of suction through the shaft 15. When the inlet 50 is substantially covered, suction commences through the end portion 60 of the nozzle 40 and into the body cavity. When the inlet 50 is substantially uncovered, suction through the end portion 60 of the nozzle 40 is removed or reduced.

While the inlet 50 is shown as a raised structure relative to the exterior surface of the shaft 15, in various embodiments of the present invention, the inlet 50 may be flush or depressed relative to the exterior surface of the shaft 15. Additionally, while the inlet 50 shown includes a flap 62 surrounding the inlet 50, the inlet 50 need only be an aperture in communication with the channel 35 of the shaft 15 and therefore need hot include the flap 62.

The handpiece 10 also includes a conduit 70. The conduit 70 includes a first end 80 and a second end 90 distal from the first end 80. The conduit 70 may be of any number of lengths or diameters. In one embodiment, the conduit 70 is of a diameter comparable to that of a 5 French feeding tube. In some embodiments, a connector 95 is coupled to the conduit 70. The connector 95 may provide a path from the conduit 70 to an irrigation source (not shown). The connector 95 may be any mechanism for coupling the conduit 70 to an irrigation source.

The conduit 70 is disposed to receive in a first end 80 of the conduit 70 an irrigation solution and to output a received irrigation solution from the second end 90 of the conduit 70. The conduit 70 has a first end 80 disposed to receive a volume of irrigation solution after one or more fingers of the single hand of the primary caregiver act upon an irrigation source proximate to the conduit 70.

The conduit 70 may be coupled to the exterior surface of the nozzle 40. The conduit 70 may be coupled to the nozzle 40 through any suitable method, including, but not limited to, a mechanical coupler (not shown), welding (not shown) or adhesive (not shown). Additionally, the conduit 70 may be connected in a temporary or permanent fashion to the nozzle 40.

Accordingly, when the conduit 70 is positioned near the body cavity of a patient, it may be used to irrigate the body cavity with an irrigation solution. The conduit 70 may be positioned in substantially the same direction as the nozzle 40 such that when the nozzle 40 is inserted into the body cavity of the patient, the conduit 70 provides a path for irrigation through the conduit 70 into the body cavity of the patient.

Although in the embodiment shown, the conduit 70 is coupled to the exterior of the nozzle 40, the conduit 70 may be coupled to the exterior of any portion of the handpiece 10 such that a body cavity is able to be irrigated using the conduit 70.

The nozzle 40 and conduit 70 are disposed to be inserted into one or more of a nose, a mouth, an ear or any other suitable body cavity. Accordingly, the primary caregiver may select and apply a nozzle 40 and/or conduit 70 having dimensions appropriate for the patient being treated. For example, the selected nozzle 40 may be a nozzle 40 appropriate for insertion into a body cavity of a baby (premature, neonate or otherwise), a child or an adult.

Accordingly, the device advantageously provides separate passageways for irrigation and suction such that the irrigation solution is not tainted by the fluid suctioned through the channel 35 of the shaft 15. Accordingly, the device reduces the likelihood of re-introduction of contaminated fluid into the body cavity of the patient.

Figure 2:
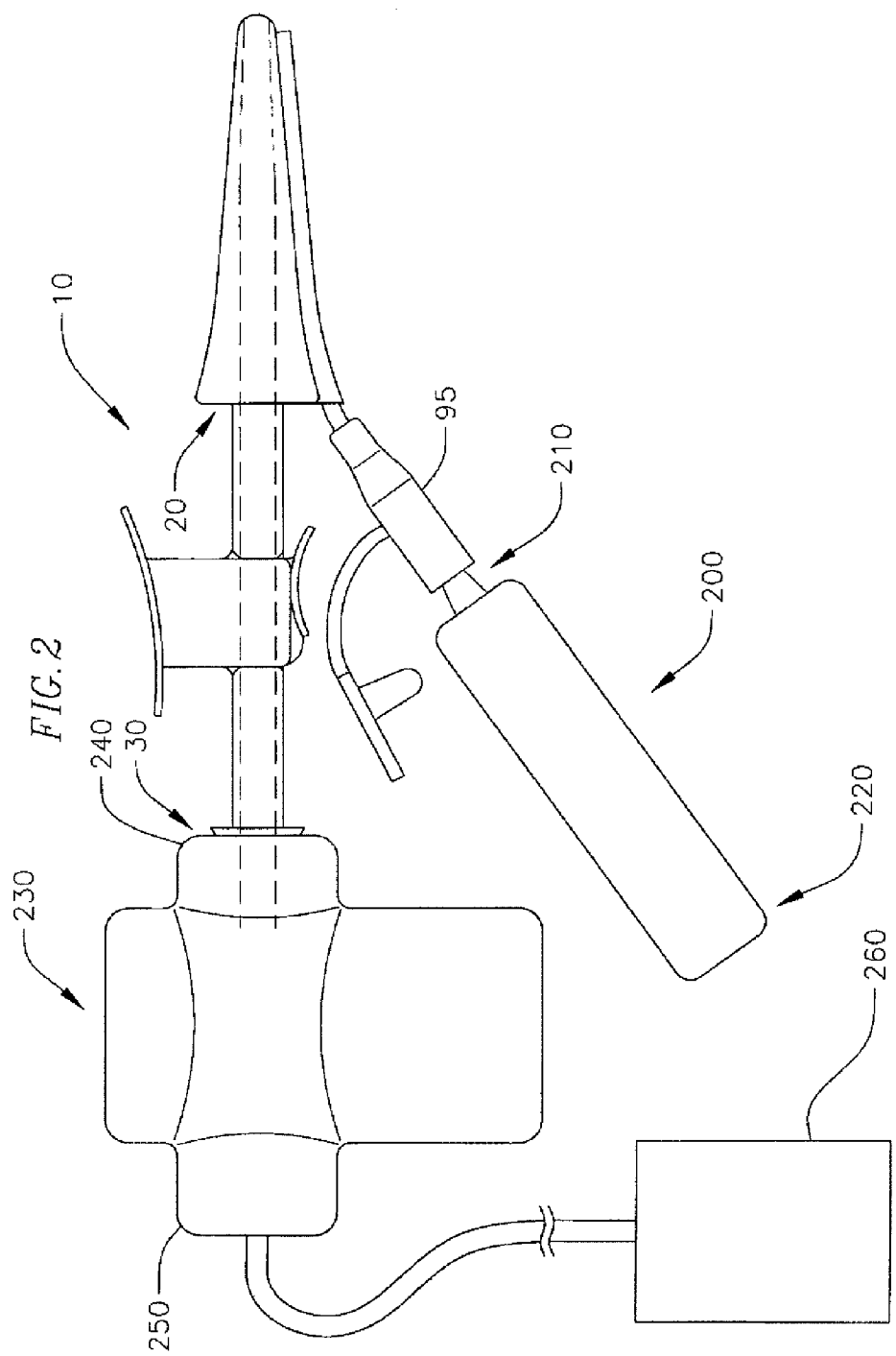
FIG. 2 is a side view of a finger-controlled combination irrigation and suction system according to one embodiment of the present invention.

FIG. 2 is a side view of a finger-controlled irrigation and suction system according to one embodiment of the present invention. The system includes the handpiece 10 of FIG. 1. In various embodiments, the system also includes one or more of an irrigation source 200, a receptacle 230 or a suction mechanism 260.

The irrigation source 200 has a first end 210 and a second end 220 distal from the first end 210. The first end 210 of the irrigation source 200 is coupled to the first end of the conduit. In some embodiments, the irrigation source 200 is coupled to the first end of the conduit via connector 95. The connector 95 may be any mechanism for coupling the conduit to an irrigation source 200. The irrigation source 200 is disposed to contain irrigation solution used to irrigate the body cavity.

In some embodiments, the irrigation source 200 is formed of a material allowing the irrigation source 200 to be manipulated with one or more of other fingers on the single hand of the primary caregiver for controlling injection of irrigation solution with the handpiece 10. In one embodiment, the irrigation source 200 is composed of a material that is easily depressed with human fingers. In some embodiments, acting upon the irrigation source 200 includes depressing the irrigation source 200 with one or more fingers of the single hand of the primary caregiver. The irrigation source 200, upon being depressed, decreases in volume and causes irrigation solution to escape from the first end 210 of the irrigation source 200.

In some embodiments, the irrigation source 200 is an ampule disposed to contain a volume of irrigation solution. The ampule may be a 5 milliliter (ml) round or a 5 ml rectangle ampule. The ampule may be a 3-5 ml plastic container. In some embodiments, the irrigation solution is saline solution. The irrigation solution may be a solution of 0.9% saline, which is often referred to as a "normal saline" solution. The irrigation solution may be a solution that is approximately the same the human body's saline concentration. The ampule may be composed of a substantially transparent material allowing the primary caregiver to observe the amount of irrigation solution injected into the conduit, whether any irrigation solution is in the irrigation source 200 or if the irrigation source 200 is empty.

In some embodiments, the irrigation source 200 contains saline solution. In other embodiments, the irrigation source 200 may contain any fluid suitable for irrigating a body cavity, including, but not limited to, water, gases or aerosols.

In some embodiments, the irrigation source 200 may be integrally formed with the handpiece 10. In some embodiments, the irrigation source 200 may include a dispensing mechanism (not shown) disposed to be coupled to the first end 210 of the irrigation source 200 to provide one or more of a spray, droplet or stream of the irrigation solution. The dispensing mechanism may be coupled to the irrigation source 200. Accordingly, the dispending mechanism may provide a spray, droplet or a stream of fluid with the handpiece 10 as decided by the caregiver.

In some embodiments, the system includes a receptacle 230. In one embodiment, the receptacle 230 includes a first port 240 disposed to be coupled to the second end 30 of the shaft 15 and a second port 250 disposed to be coupled to a suction mechanism 260. The receptacle 230 is disposed to receive through its first port 240 fluid suctioned through the shaft 15 and to retain such suctioned fluid. In various embodiments, the receptacle 230 includes only a single port. In one embodiment, the receptacle 230 is coupled to the second end of the shaft 15 with one or more connectors (not shown). Accordingly, suction may be provided along a path from a suction mechanism 260 coupled to the second port 250 of the receptacle 230 through the receptacle 230 through the nozzle of the handpiece 10 and from the body cavity of the patient (not shown).

In embodiments of the receptacle 230 having a first port 240 and a second port 250, the first port 240 and the second port 250 may be positioned to be at different heights along the exterior surface of the receptacle 230 such that fluid may fall into the receptacle 230 and be maintained therein and not be suctioned into the suction mechanism 260. In one embodiment, the receptacle 230 includes a first port 240 that is lower in height than a second port 250 wherein the first port 240 is coupled to the handpiece 10 and the second port 250 is coupled to the suction mechanism 260. In various embodiments, the receptacle 230 may be a specimen cup, a sputum tap, a luki tube or any container for receiving and retaining fluid suctioned through the shaft 15.

Accordingly, the system may be used to retrieve and retain fluid for laboratory testing. For example, nasal secretions may be collected for identification of disease organisms. Generally, samples may be collected for culture and sensitivity tests.

In some embodiments, the system includes a suction mechanism 260. In one embodiment, the suction mechanism 260 is coupled to the second end 30 of the shaft 15. The suction mechanism 260 may be coupled to the shaft 15 with a tube. In some embodiments, the suction mechanism 260 is connected directly to the shaft 15. The suction mechanism 260 may be any machine disposed to provide suction force. The suction mechanism 260 may be electric or pneumatic powered. The suction mechanism 260 may provide 80-100 cm $H_2O$ suction pressure.

Figure 3:
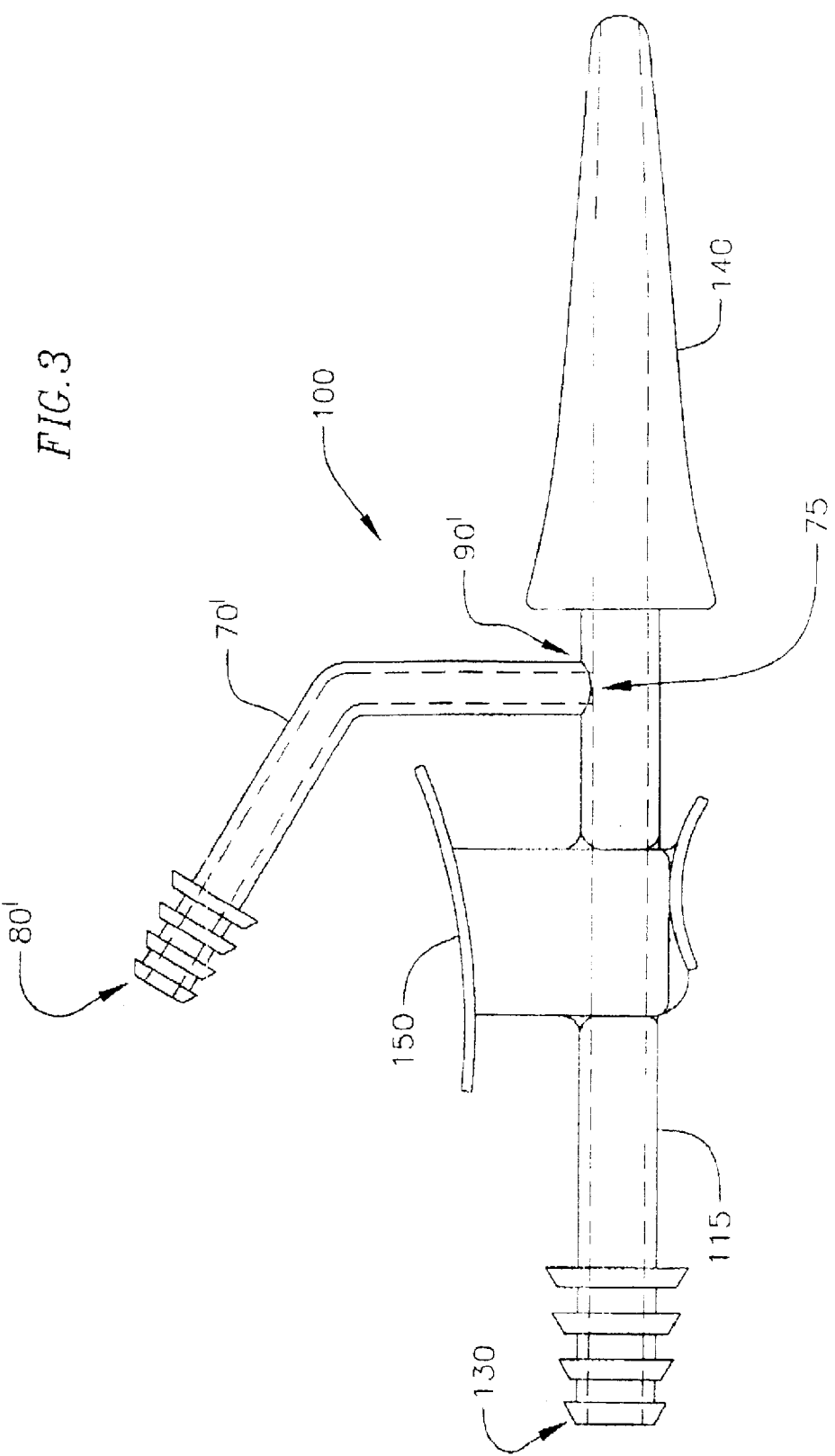
FIG. 3 is a side view of a finger-controlled combination irrigation and suction device of a finger-controlled system according to another embodiment of the present invention.

FIG. 3 is a side view of a finger-controlled combination irrigation and suction device of a finger-controlled system according to another embodiment of the present invention. The system of FIG. 3 includes a handpiece 100 having a shaft 115, an inlet 150 and a nozzle 140 similar to that of FIG. 1.

The handpiece 100 also includes a conduit 70'. The conduit 70' includes a first end 80' and a second end 90' distal from the first end 80'. The second end 90' of the conduit 70' is coupled to a second inlet 75 in the shaft 115 of the handpiece 100 such that the channel of the shaft 115 is in communication with the conduit 70'.

With reference to FIG. 3, the conduit 70' may be of any number of lengths or diameters. The conduit 70' may be coupled to the shaft 115 through any suitable methods, including, but not limited to, a mechanical coupler (not shown) or adhesive (not shown). Additionally, the conduit 70' may be connected in a temporary or permanent fashion to the shaft 115. The conduit 70' may be integrally formed with the shaft 115.

The conduit 70' is disposed to receive in a first end 80' of the conduit 70' an irrigation solution and to output the received irrigation solution from a second end 90' of the conduit 70'. The conduit 70' has a first end 80' disposed to receive a volume of irrigation solution after one or more fingers of the single hand of the primary caregiver act upon an irrigation source (not shown) proximate to the conduit 70'.

Accordingly, the conduit 70' may deliver irrigation solution along a path from the second inlet 75 of the shaft 115 through the nozzle 140 and into the body cavity. Accordingly, a primary caregiver can provide irrigation and suction using the fingers of a single hand of the primary caregiver.

The nozzle 140 is disposed to be inserted into one or more of a nose, a mouth, an ear or any other suitable body cavity. Accordingly, the primary caregiver may select and apply a nozzle 140 having dimensions appropriate for the patient being treated. For example, the selected nozzle 140 may be a nozzle 140 appropriate for insertion into a body cavity of a baby (premature, neonate or otherwise), a child or an adult.

Accordingly, the device advantageously provides fast irrigation and suction of a body cavity using only the single hand of a primary caregiver.

Figure 4:
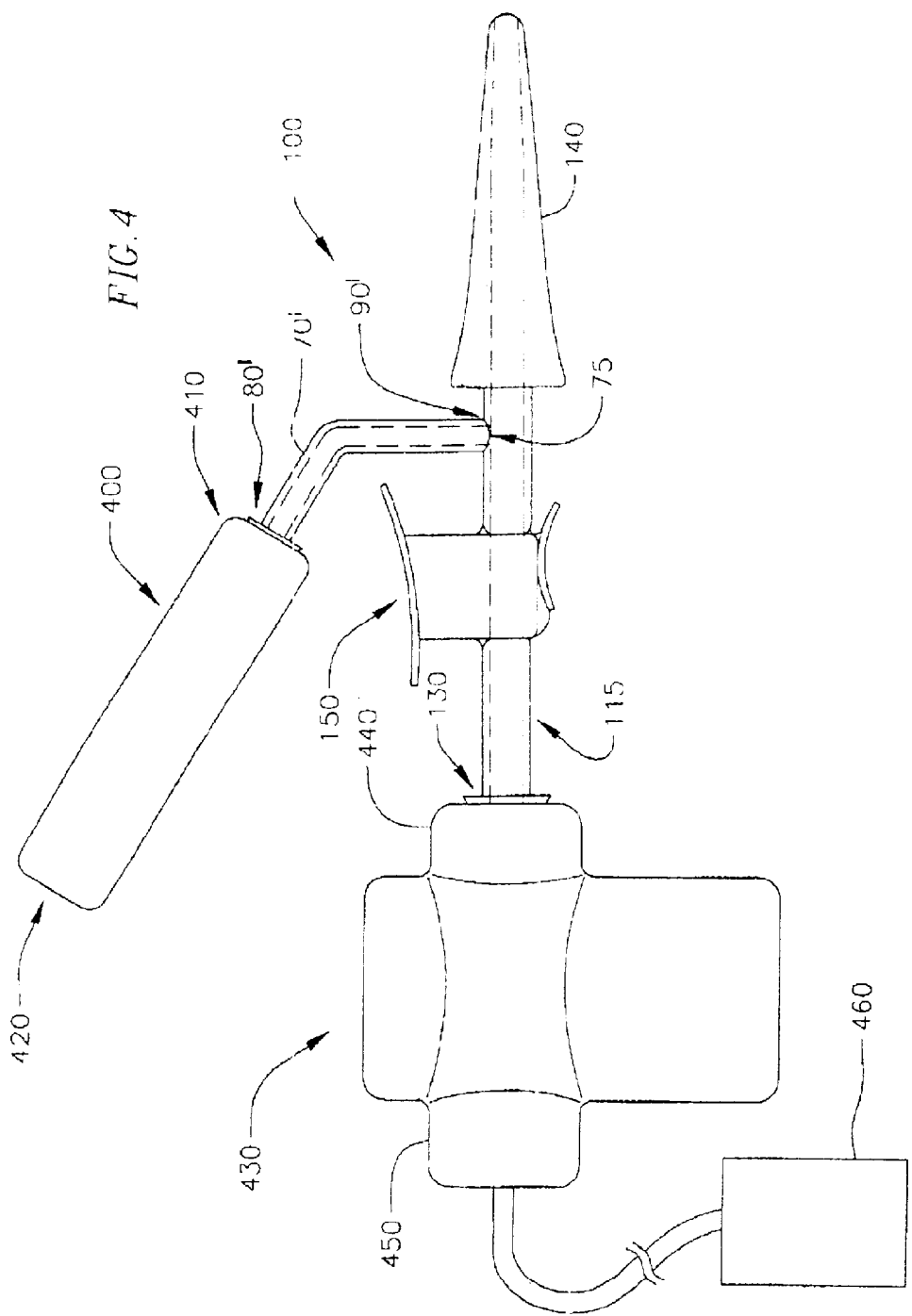
FIG. 4 is a side view of a finger-controlled combination irrigation and suction system according to another embodiment of the present invention.

FIG. 4 is a side view of a finger-controlled irrigation and suction system according to another embodiment of the present invention. The system of FIG. 4 includes components similar to those of FIG. 3 and one or more of the receptacle 430, irrigation source 400 or suction mechanism 460 similar to that of FIG. 2.

The system of FIG. 4 includes handpiece 100 of FIG. 3. In various embodiments, the system also includes one or more of an irrigation source 400, a receptacle 430 or a suction mechanism 460.

The irrigation source 400 has a first end 410 and a second end 420 distal from the first end 410. The first end 410 of the irrigation source 400 is coupled to the first end 80' of the conduit 70'. The irrigation source 400 is disposed to contain irrigation solution used to irrigate the body cavity.

In some embodiments, the irrigation source 400 is formed of a material allowing the irrigation source 400 to be manipulated with one or more of other fingers on the single hand of the primary caregiver for controlling injection of irrigation solution with the handpiece 100. In one embodiment, the irrigation source 400 is composed of a material that is easily depressed with human fingers. In some embodiments, acting upon the irrigation source 400 includes depressing the irrigation source 400 with one or more fingers of the single hand of the primary caregiver. The irrigation source 400, upon being depressed, decreases in volume and causes irrigation solution to escape from the first end 410 of the irrigation source 400.

In some embodiments, the irrigation source 400 is an ampule disposed to contain a volume of irrigation solution. The ampule may be composed of a substantially transparent material allowing the primary caregiver to observe the amount of irrigation solution injected into the conduit 70', whether any irrigation solution is in the irrigation source 400 or if the irrigation source 400 is empty.

In some embodiments, the irrigation source 400 contains saline solution. In other embodiments, the irrigation source 400 may contain any fluid suitable for irrigating a body cavity, including, but not limited to, water, gases or aerosols.

In some embodiments, the irrigation source 400 may be integrally formed with the handpiece 100. In some embodiments, the irrigation source 400 may include a dispensing mechanism (not shown) disposed to be connected to the first end 410 of the irrigation source 400 to provide a spray, droplet or stream of the irrigation solution. The dispensing mechanism may be coupled to the irrigation source 400. Accordingly, the dispending mechanism may provide a spray, droplet or a stream of fluid with the handpiece 100 as decided by the caregiver.

In some embodiments, the system includes a receptacle 430. In one embodiment, the receptacle 430 includes a first port 440 disposed to be coupled to the second end 130 of the shaft 115 and a second port 450 disposed to be coupled to a suction mechanism 460. The receptacle 430 is disposed to receive through its first port 440 fluid suctioned through the shaft 115 and to retain such suctioned fluid. In various embodiments, the receptacle 430 includes only a single port. In one embodiment, the receptacle 430 is coupled to the second end 130 of the shaft 115 with one or more connectors (not shown). Accordingly, suction may be provided along a path from a suction mechanism 460 coupled to the second port 450 of the receptacle 430 through the receptacle 430 through the nozzle 140 of the handpiece 100 and from the body cavity of the patient (not shown).

In embodiments of the receptacle 430 having a first port 440 and a second port 450, the first port 440 and the second port 450 may be positioned to be at different heights along the exterior surface of the receptacle 430 such that fluid may fall into the receptacle 430 and be maintained therein and not be suctioned into the suction mechanism 460. In one embodiment, the receptacle 430 includes a first port 440 that is lower in height than a second port 450 wherein the first port 440 is coupled to the handpiece 100 and the second port 450 is coupled to the suction mechanism 460. In various embodiments, the receptacle 430 may be a specimen cup, a sputum tap, a luki tube or any container for receiving and retaining fluid suctioned through the shaft 115.

Accordingly, the system may be used to retrieve and retain fluid for laboratory testing. For example, nasal secretions may be collected for identification of disease organisms. Generally, samples may be collected for culture and sensitivity tests.

In some embodiments, the system includes a suction mechanism 460. In one embodiment, the suction mechanism 460 is coupled to the second end 130 of the shaft 115. The suction mechanism 460 may be coupled to the shaft 115 with a tube. In some embodiments, the suction mechanism 460 is connected directly to the shaft 115. The suction mechanism 460 may be any machine disposed to provide suction force. The suction mechanism 460 may provide 80-100 centimeters (cm) $H_2O$ suction pressure. The suction mechanism 460 may be electric or pneumatic powered.

A method of using the embodiments of the finger-controlled irrigation and suction systems and devices of FIGS. 1-4 includes holding the handpiece in a first hand of a primary caregiver such that the primary caregiver has at least one finger that can be manipulated to cover the inlet on the exterior surface of the shaft, and at least one finger to depress the irrigation source. The finger for covering the inlet may be the same finger for depressing the irrigation source or the fingers may be different. For example, the primary caregiver may alternate between using the thumb for covering and uncovering the inlet and for depressing the irrigation source. In another example, the primary caregiver may use the thumb for covering and uncovering the inlet and the index finger for depressing the irrigation source. The primary caregiver may use any finger or combination thereof for operating the device.

The suction mechanism is coupled to the second end of the handpiece and turned on to provide suction force in the handpiece. The first end of the conduit is coupled to the irrigation source such that the irrigation source is positioned to output a volume of irrigation solution with the handpiece after the irrigation source is depressed.

The nozzle of the handpiece is placed in close proximity to the body cavity at which irrigation and suction is desired. At the option of the primary caregiver, the nozzle may be placed inside the body cavity to a desired depth.

The primary caregiver uses a finger of the hand in which the handpiece is positioned to depress the irrigation source thereby injecting a volume of irrigation solution with the handpiece. The irrigation solution travels into the body cavity of the patient. Accordingly, the body cavity of the patient is irrigated. The consistency of the fluid may change in response to the type of the irrigation solution. For example, when the irrigation solution is a saline solution, the fluid may develop a consistency that is thinner than the consistency that the fluid prior to irrigation.

The primary caregiver uses a finger of the hand in which the handpiece is positioned to cover the inlet thereby causing suction to occur at the nozzle of the handpiece. Accordingly, fluid is suctioned from the body cavity that is in close proximity to the nozzle. The primary caregiver removes the finger of the hand in which the handpiece is positioned thereby uncovering the inlet to reduce or substantially remove suction at the nozzle. The primary caregiver may also partially cover or uncover the inlet to vary the amount of suction pressure at the nozzle.

Accordingly, the device allows a primary caregiver to perform irrigation and suction with a single hand and without the aid of a secondary caregiver. Therefore, a primary caregiver can hold a baby, infant or child with one arm and hand and provide both irrigation and suction with the other hand without the aid of a secondary caregiver. Further, simple finger control of the irrigation and suction device allows a primary caregiver to provide irrigation and suction in a short amount of time. Additionally, the primary caregiver can vary the amount of irrigation provided to the body cavity by taking into account one or more of the following factors: an appropriate amount of pressure depending on the volume of irrigation solution in the irrigation source or the length or diameter of the conduit.

The foregoing steps may be performed in any order at the discretion of the primary caregiver. For example, the primary caregiver may position the nozzle in close proximity to the body cavity with the inlet covered, uncovered or partially covered.

Figure 5:
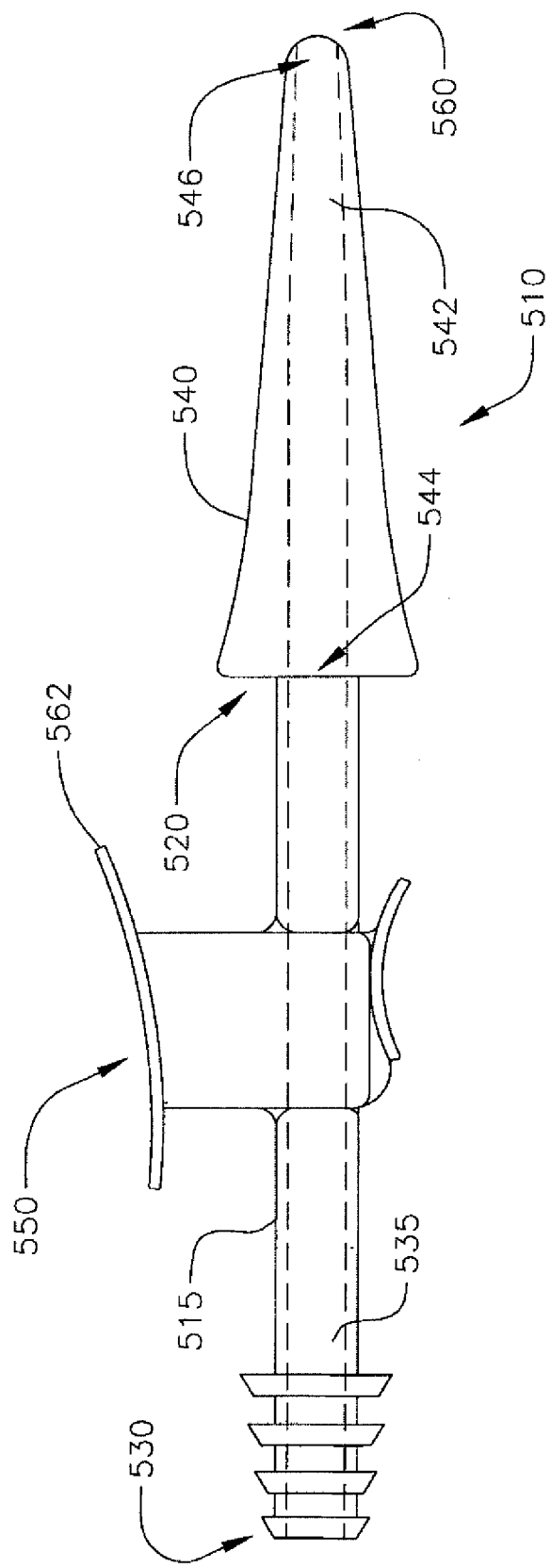
FIG. 5 is a side view of a finger-controlled suction device of a finger-controlled suction system according to one embodiment of the present invention.

FIG. 5 is a side view of a finger-controlled suction device of a finger-controlled system according to one embodiment of the present invention. The finger-controlled suction system includes a handpiece 510 having a shaft 515, an inlet 550 and a nozzle 540 similar to that of FIG. 1.

The handpiece 510 is a portable device disposed to provide suction of a body cavity. The handpiece 510 is disposed to be held and easily manipulated in the hand of a primary caregiver. The handpiece 510 may be held in a first hand of the primary caregiver while the primary caregiver holds or restrains a patient with a second hand of the primary caregiver.

The handpiece 510 includes a shaft 515, a nozzle 540 and an inlet 550. The shaft 515 includes a first end 520 and a second end 530 distal from the first end 520. The shaft 515 also includes a channel 535 disposed from the first end 520 of the shaft 515 to the second end 530 of the shaft 515 for allowing suction force through the shaft 515 between the first end 520 of the shaft 515 and the second end 530 of the shaft 515. In various embodiments, the first end 520 and/or the second end 530 may have a smooth or ribbed exterior surface facilitating attachment of one or more other components or devices to the shaft 515.

The shaft 515 may be composed of a rigid material, including but not limited to, hardened plastic or glass. Although the embodiment of the handpiece 510 shown illustrates the shaft 515 as elongated and tubular, other designs are possible and are envisaged within the scope of this patent application. In one or more embodiments, the shaft 15 may be any number of shapes that may be held in a single hand of a single caregiver and finger-controlled, including, but not limited to, cube- or dome-shaped.

The handpiece 510 also includes a nozzle 540 coupled to the first end 520 of the shaft 515. The nozzle 540 may be permanently or temporarily coupled to the first end 520 of the shaft 515 through any number of suitable methods. In various embodiments, the nozzle 540 may be welded, joined with adhesive or telescopically coupled to the shaft 515. Additionally, the nozzle 540 may include ridges on the interior of its surface for coupling to ridges of shaft 515.

The nozzle 540 is pliable. In various embodiments, the nozzle 540 is composed substantially of rubber, soft plastic or other pliable material. The nozzle 540 is generally conical-shaped. In various embodiments, the conical-shape may be more slender or less slender. Accordingly, an angle from an end portion 560 of the nozzle 540 to a point on the exterior surface of the nozzle 540 may vary depending on the design of the nozzle 40 and all such variations are envisaged. The nozzle 540 may be coupled to the shaft 515 by any suitable methods, including, but not limited to, welding, screw-on attachment or telescopic attachment.

A channel 542 of the nozzle 540 is located through the nozzle 540 wherein the first end 544 of the channel 542 of the nozzle 540 is in communication with the channel 535 of the shaft 515 and the second end 546 of the channel of the nozzle 540 is positioned near the end portion 560 of the nozzle 540 thereby creating a path for flow of suction force from the second end 30 of the shaft 515 to the end portion 560 of the nozzle 540.

The end portion 560 includes an end portion inlet (not shown) through the end portion 560 from the channel 542 to the outside environment. The end portion inlet in the end portion 560 of the nozzle 540 may be any number of diameters that can provide adequate suction and allow fluids of thick consistency, such as meconium secretions, to travel through the nozzle 540 and into the channel 535 of the shaft 515. Accordingly, when the end portion of the nozzle 540 is provided in close proximity to a body cavity, suction force may be provided to the body cavity through the end portion 560 of the nozzle 540.

The diameter of the end portion 560 and/or the exterior of the nozzle 540 generally may be any number of diameters. Accordingly, a nozzle 540 may be selected according to its design wherein the caregiver may take into account the age and/or medical condition of the patient.

In various embodiments, the end portion 560 may be of any design such that the end portion 560 may meet with a body or body cavity and the likelihood of injury is relatively low. In various embodiments, the end portion 560 is substantially round or substantially flat in configuration. The substantially round and substantially flat configurations may be designed with curvature of various degrees such that one end portion 560 may be designed to be more circular or more angular than other configurations. Similarly, the flat configuration may be somewhat convex, concave or otherwise.

The handpiece 510 also includes an inlet 550 in the exterior surface of the shaft 515. The inlet 550 is in operable communication with the channel 535 of the shaft 515. The inlet 550 is shown located approximately midway between the first end 520 and the second end 530 of the shaft 515 but may be located at any position along the shaft 515 allowing a primary caregiver to cover the inlet 550 with one or more fingers of the single hand of the primary caregiver. The inlet 550 is disposed to be manually covered and uncovered by one or more fingers of a single hand of a primary caregiver for control of suction through the shaft 515. When the inlet 550 is substantially covered, suction commences through the end portion 560 of the nozzle 540 and into the body cavity. When the inlet 550 is substantially uncovered, suction through the end portion 560 of the nozzle 540 is removed or reduced.

While the inlet 550 is shown as a raised structure relative to the exterior surface of the shaft 515, in various embodiments of the present invention, the inlet 550 may be flush or depressed relative to the exterior surface of the shaft 515. Additionally, while the inlet 550 may include a flap 562 surrounding the inlet 550, the inlet 550 need only be an aperture in communication with the channel 535 of the shaft 515 and therefore need not include the flap 562.

A method of using the finger-controlled suction device includes the following steps. The primary caregiver holds the handpiece in a first hand of the primary caregiver such that the primary caregiver has at least one finger that can be manipulated to cover the inlet in the exterior surface of the shaft. The suction mechanism is coupled to the second end of the handpiece and turned on to provide suction force in the handpiece. The nozzle of the handpiece is placed in close proximity to the body cavity from which suction is desired. At the option of the primary caregiver, the nozzle may be placed inside the body cavity to a desired depth. The primary caregiver uses a finger of the hand in which the handpiece is positioned to cover the inlet thereby causing suction to occur at the nozzle of the handpiece. Accordingly, fluid is suctioned from the body cavity that is in close proximity to the nozzle. The suctioned fluid may be received and retained by a receptacle in some embodiments. The primary caregiver removes the finger of the hand in which the handpiece is positioned thereby uncovering the inlet to reduce or substantially remove suction at the nozzle. The primary caregiver may also partially cover the inlet to vary the amount of suction pressure at the nozzle.

The foregoing steps may be performed in any order at the discretion of the primary caregiver. For example, the primary caregiver may position the nozzle in close proximity to the body cavity with the inlet covered, uncovered or partially covered.

Accordingly, the finger-controlled suction device allows a primary caregiver to perform suction with a single hand and without the aid of a secondary caregiver. Therefore, a primary caregiver can hold a baby, infant or child with one arm and hand and provide suction with the other hand without the aid of a secondary caregiver. Further, simple finger control of the finger-controlled suction device allows a primary caregiver to provide suction in a short amount of time. Additionally, the primary caregiver can vary the amount of suction pressure to an appropriate amount of pressure depending on the age or medical needs of the patient.

FIGS. 6, 7, 8, 9, 10, 11, 12 and 13 are views of mere exemplary finger-controlled handpieces according to embodiments of the present invention. While the embodiments include dimensions for one or more components of the handpiece, it is recognized by the inventor and those skilled in the art that suitable dimensions for one or more components of the handpiece may be dictated by the designer and may vary from the dimensions described below in FIGS. 6-13, and all such variations are envisaged within this application.

Figures 6, 7, 8:
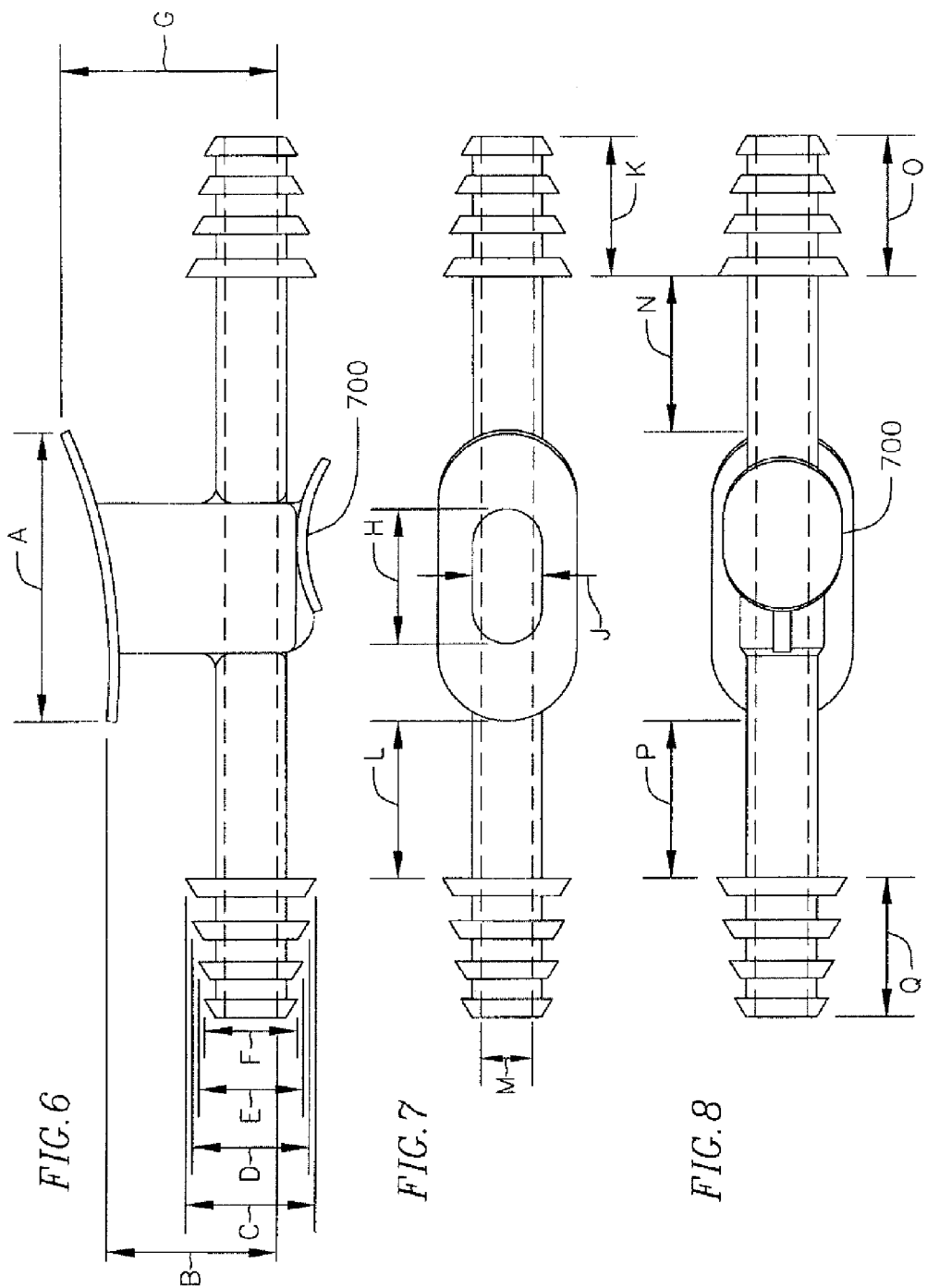
FIGS. 6, 7, 8, 9, 10, 11, 12 and 13 are views of mere exemplary finger-controlled handpieces according to embodiments of the present invention.

FIG. 6 is a side view of a finger-controlled handpiece according to an embodiment of the invention. With all measurements in millimeters unless otherwise noted, the length of the flap, A, is 26, the heights of ridges C, D, E and F are 11, 10, 8 and 6, respectively, with the mirror of the ridges on the opposite side of the handpiece. In the embodiment shown, on the left side of the handpiece, the width from the outer edge of the leftmost ridge to the outermost edge of the rightmost ridge is 8. The width of the rightmost ridge on the left side of the handpiece is 10. The same dimensions are provided for the corresponding ridge widths on the right side of the handpiece.

The height from the bottom of the channel of the shaft to the lower portion of the flap, B, is 16. The height from the bottom of the channel of the shaft to the higher portion of the flap, G, is 19. A finger rest 700 is provided for resting the hand of the primary caregiver in order to hold the handpiece in a stable position.

FIG. 7 is a top view of a finger-controlled handpiece according to an embodiment of the invention. With all measurements in millimeters unless otherwise noted, the height of the inlet, J, is 6 while the width of the inlet, H, is 12. The length between a first edge of the flap and a location at which ridges begin, L, is 20, the width of the region of the ridges, K, is 13. The width of the region of the ridges is approximately the same for the region on the left side and on the right side of the handpiece. The height of the channel through the shaft, M, is 3, which is also approximately 5/32nd of an inch.

FIG. 8 is a bottom view of a finger-controlled handpiece according to an embodiment of the invention. With all measurements in millimeters unless otherwise noted, the width between a first edge of a flap and a location at which ridges begin on the left side of the handpiece, P, is 20. The width between a second edge of a flap and a location at which ridges begin on the right side of the handpiece, N, is 20. The width of the region of the ridges is approximately the same for the region on the left side of the handpiece, Q, and on the right side of the handpiece, O, and is 13 mm each. A finger rest 700 is provided for resting the hand of the primary caregiver in order to hold the handpiece in a stable position.

Figure 9:
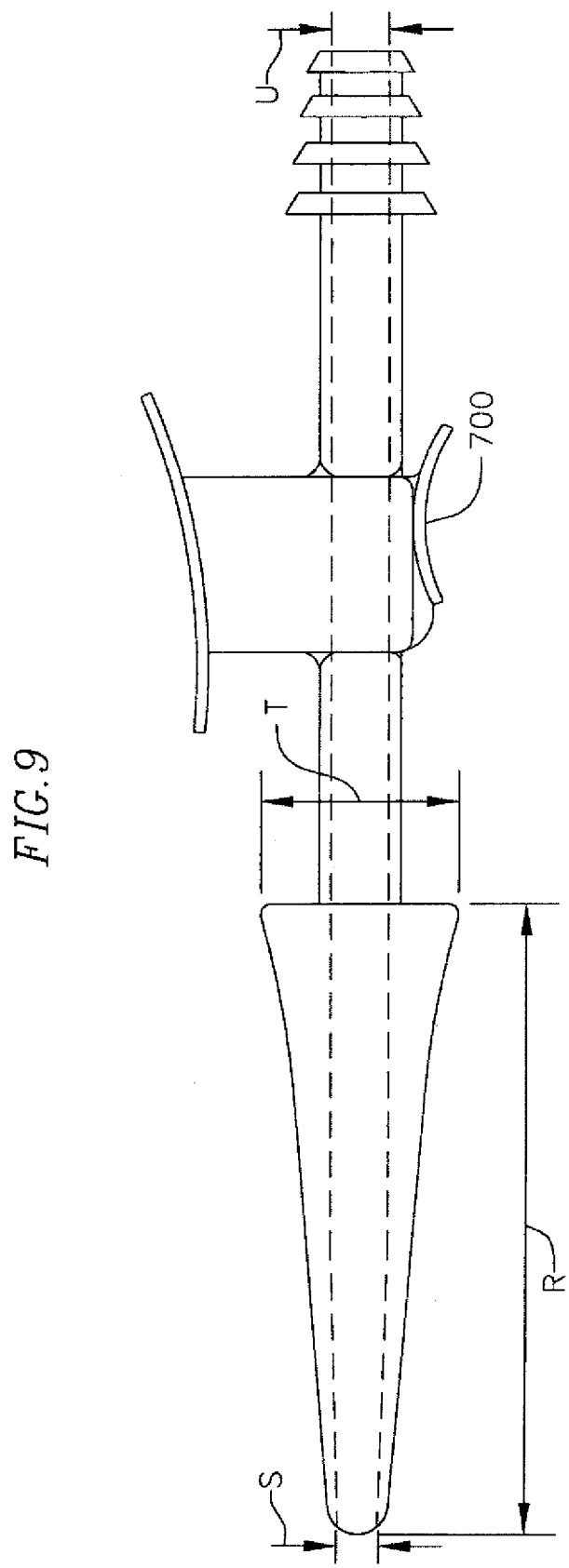

FIG. 9 is a side view of a finger-controlled handpiece according to another embodiment of the invention. With all measurements in millimeters unless otherwise noted, the height of the channel through the nozzle, S, is 3. The height of the wider edge of the nozzle, T, is 15. The length of the nozzle, R, is 50. The height of the channel through the shaft, U, is 3. A finger rest 700 is provided for resting the hand of the primary caregiver in order to hold the handpiece in a stable position.

Figures 10, 11, 12, 13:
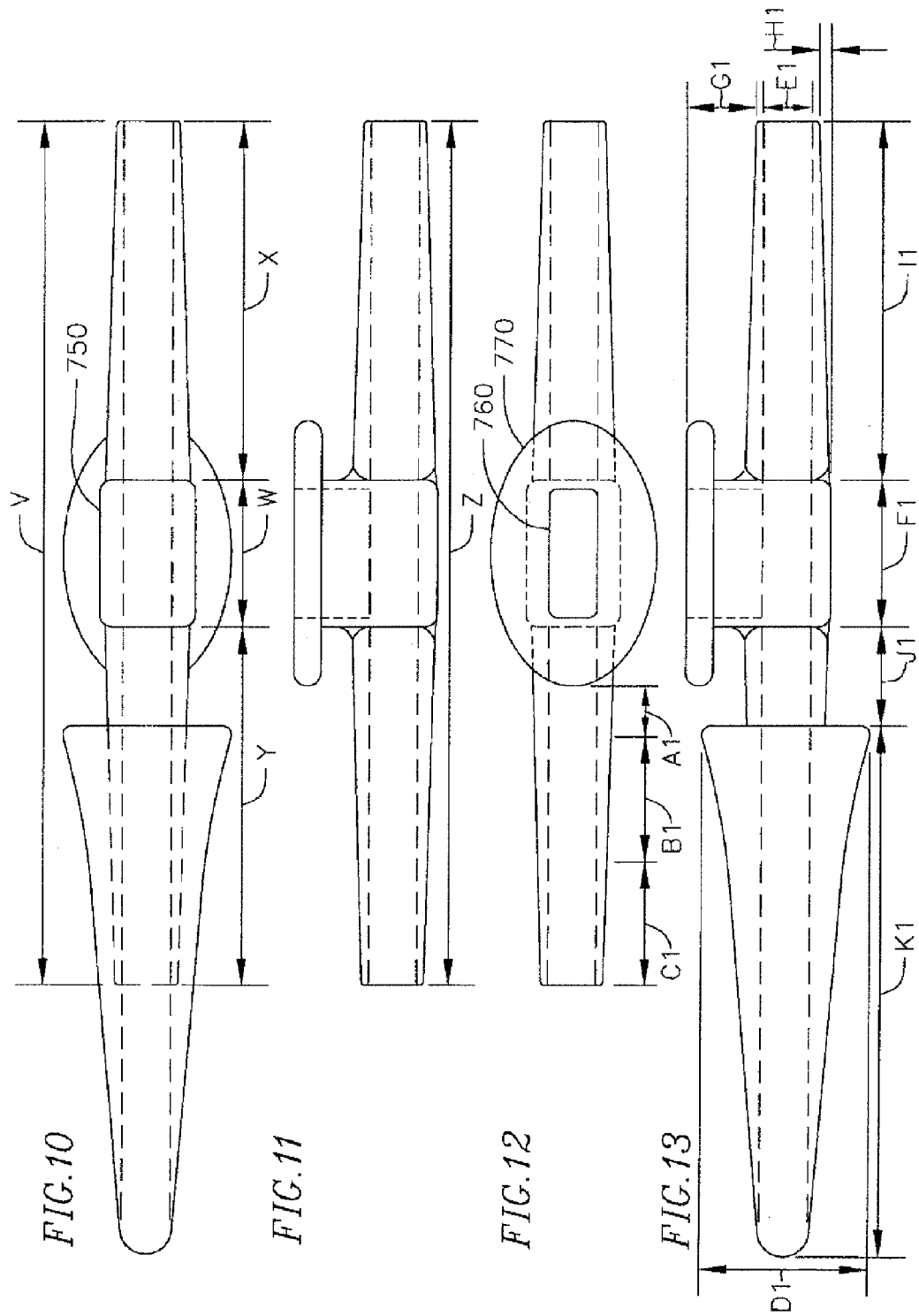

FIG. 10 is a bottom view of a finger-controlled handpiece according to another embodiment of the invention. With all measurements in millimeters unless otherwise noted, the length from a first end of the handpiece to a selected position on the nozzle, V, is 75. A finger rest 750 is provided for resting the hand of the primary caregiver in order to hold the handpiece in a stable position. The length of the finger rest, W, is 45. The length from the first end of the handpiece to a first edge of the finger rest, X, is 30. The length from the selected position on the nozzle to a second edge of the finger rest, Y, is 30.

FIG. 11 is a side view of a finger-controlled handpiece according to another embodiment of the invention. With all measurements in millimeters unless otherwise noted, the length of the shaft of the handpiece, Z, is 75.

FIG. 12 is a top view of a finger-controlled handpiece according to another embodiment of the invention. With all measurements in millimeters unless otherwise noted, the length of various portions of the shaft of the handpiece, A1, B1 and C1, are each 10. An inlet 760 is provided in a flap 770.

FIG. 13 is a side view of a finger-controlled handpiece according to another embodiment of the invention. With all measurements in millimeters unless otherwise noted, the height of the wider edge of the nozzle, D1, is 15. The length of the nozzle, K1, is 50. The length of the region between the edge of the nozzle and to a first edge of the inlet, J1, is 5. The length of the inlet, F1, is 10. The length from a second edge of the inlet to a first edge of the shaft of the handpiece, I1, is 30. The height from the top of a first edge of the shaft of the handpiece to the top of the flap, G1, is 10. The height of the channel through the shaft, E1, is 5, which is approximately 5/32nd inch. The height from the tapered bottom of the first edge of the shaft to the bottom of the first edge, H1, is 4.

Figure 14:
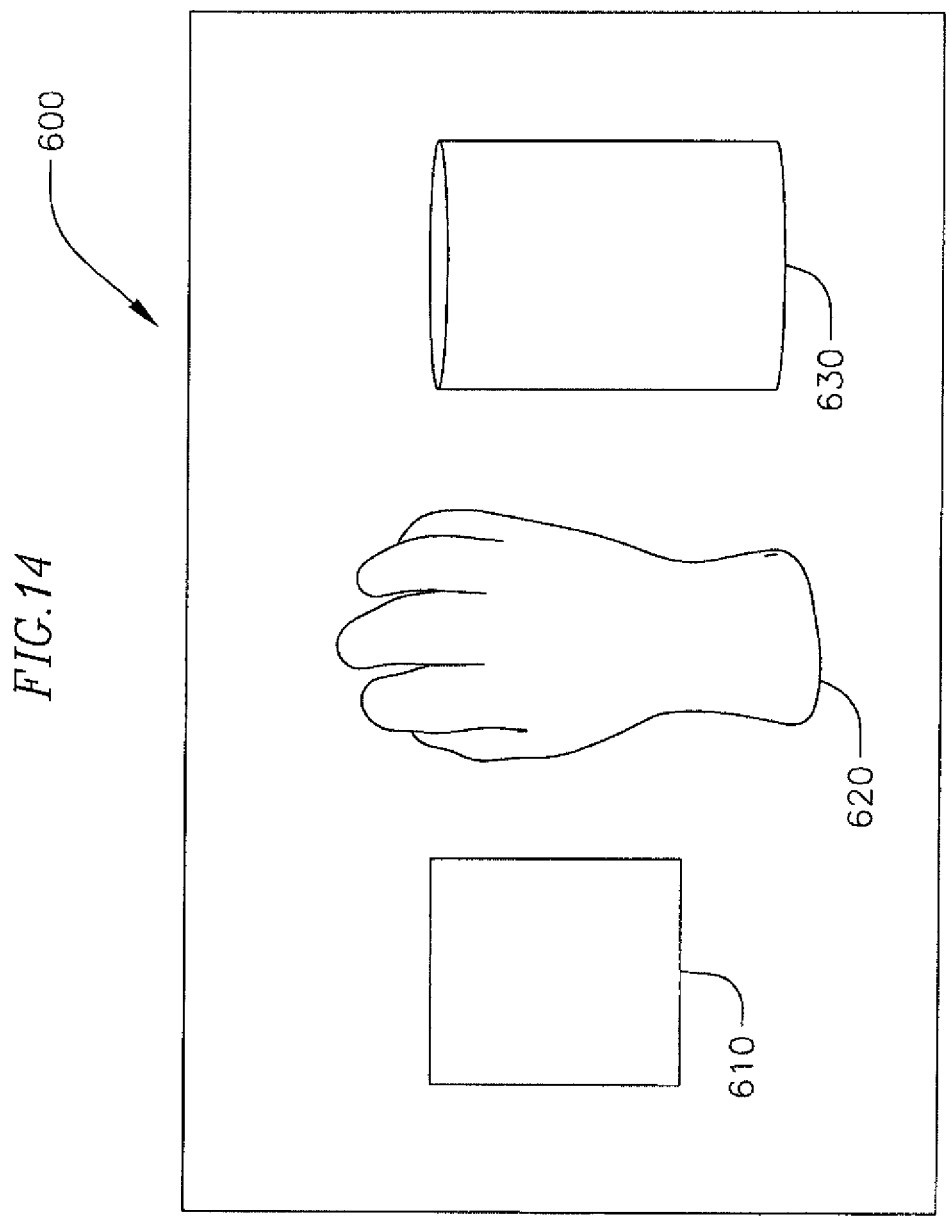
FIG. 14 is an illustration of the contents of a medical kit according to one embodiment of the present invention.

FIG. 14 is an illustration of the contents of a medical kit according to one embodiment of the present invention. In the embodiment shown, the medical kit 600 includes a medical apparatus 610, one or more medical gloves 620 and a receptacle 630.

In some embodiments, the medical apparatus is any device described with reference to any one of FIGS. 1-13 or a combination thereof. In some embodiments, referring to FIGS. 1-5, the medical apparatus is any handpiece disposed for holding the handpiece and for controlling, with a single hand of a primary caregiver, suction or irrigation and suction. In some embodiments, the medical apparatus is a finger-controlled combination irrigation and suction apparatus including a handpiece being disposed with an inlet disposed to be covered and uncovered by one or more fingers of a single hand of a primary caregiver to control suction through the handpiece and a conduit disposed to receive irrigation solution upon one or more fingers of the single hand of the primary caregiver acting upon an irrigation source proximate to the conduit.

The receptacle 630 is as described with reference to FIGS. 2 and 4. The receptacle 630 is coupleable to the medical apparatus 610 and is disposed to receive and retain fluid suctioned through the medical apparatus 610.

The medical glove is disposed to be worn by the primary caregiver. The medical glove is composed of a material allowing adherence to medical safety standards. In some embodiments, the medical glove is composed substantially of rubber.

In some embodiments, the kit also includes an irrigation source (not shown) that is coupleable to the medical apparatus 610. The irrigation source is disposed to contain an irrigation solution that may be used to irrigate a body cavity using the medical apparatus 610.

Accordingly, a one-use or multi-use medical kit is provided.

In some embodiments, any embodiment of the aforementioned handpieces shown in the figures or components thereof may have one or more swivel mechanisms to provide right handed or left handed use. The swivel mechanism may be coupled to the conduit, for example. The swivel mechanism may be coupled to the dispensing mechanism, for example.

In some embodiments, the conduit may be positioned in a different location from those disclosed to facilitate right handed or left handed use.

In any of the embodiments of the handpiece, an irrigation source holder may optionally be included. The irrigation source holder may be disposed to be coupleable to the handpiece and disposed to receive and retain the irrigation source.

While embodiments of the present invention have been described in connection with exemplary embodiments, it is to be understood that the invention is not limited to the disclosed embodiments, but, on the contrary, is intended to cover various modifications and equivalent arrangements included within the spirit and scope of the specification, appended claims and their equivalents.

What is claimed is:

1. A finger-controlled handpiece disposed to provide combined irrigation and suction, the handpiece comprising:
   a shaft having a first end and a second end distal from the first end, the shaft also having a channel disposed from the first end of the shaft to the second end of the shaft and disposed to allow suction through the shaft;
   a nozzle coupled to the first end of the shaft, wherein the nozzle is a first component of the handpiece and the shaft is a second component of the handpiece;
   an inlet disposed through an exterior surface of the shaft and in operable communication with the channel, the inlet being disposed to be manually covered and uncovered by a first portion of a single hand to control suction through the shaft wherein the inlet is sized such that an amount of the inlet that is covered is controllable to cause different suction pressures that are controllable to differ in pressure during a same operation of the finger-controlled handpiece;
   a conduit having a first end disposed to receive irrigation solution and having a second end disposed to output at least one of a spray, droplet or stream of the received irrigation solution from the conduit; and
   a dispenser coupled to the first end of the conduit and capable of alternatively outputting each of a spray, a droplet or a stream of the irrigation solution to the conduit,
   wherein whether the spray, the droplet or the stream is output is based, at least, in part, on an amount of pressure applied to a pliable irrigation source by the single hand,
   wherein the dispenser is disposed to receive irrigation solution and output the spray, droplet or stream of the irrigation solution to the conduit,
   wherein the conduit is disposed to output the spray, droplet or stream of the irrigation solution, due to positive pressure applied, from the single hand, on the pliable irrigation source that is coupled to the dispenser and that contains the irrigation solution,
   and wherein the finger-controlled handpiece can concurrently control the amount of pressure applied to the pliable irrigation source and the volume of irrigation solution emitted from the pliable irrigation source such that the amount of pressure and the volume of irrigation solution emitted from the irrigation source is modifiable during operation of the finger-controlled handpiece and such that a first form of the irrigation solution is capable of being emitted from the dispenser at a first time and a second form of the irrigation solution is capable of being emitted from the dispenser at a second time, the first time and the second time being during the operation of the finger-controlled handpiece, wherein the first form is at least one of the spray, the droplet or the stream and the second form is at least one of the spray, the droplet or the stream, wherein the finger-controlled handpiece can be controlled during operation such that the first form differs from the second form,
   wherein the dispenser and the inlet are concurrently operable by the single hand,
   and wherein concurrent operation comprises:
      causing the dispenser to receive the irrigation solution based on depression of the pliable irrigation source by at least one of a second portion of the single hand or the first portion of the single hand, and wherein the finger-controlled handpiece is configured such that manual depression by the single hand on the pliable irrigation source controls whether the first form or the second form of the irrigation solution is output from the pliable irrigation source; and
      at least one of a covering or uncovering of the inlet by the first portion of the single hand.

2. The handpiece of claim 1, wherein the nozzle is comprised of pliable material.

3. The handpiece of claim 1, wherein the shaft is comprised of a rigid material.

4. The handpiece of claim 1, wherein the second end of the conduit is in fluid communication with the channel.

5. The handpiece of claim 1, wherein the handpiece is disposable.

6. The handpiece of claim 1, wherein the nozzle is adapted for use in an oral cavity.

7. The handpiece of claim 1, wherein the nozzle is telescopically coupled to the shaft.

8. A finger-controlled handpiece disposed to provide suction and irrigation of a body cavity, the handpiece comprising:
   a shaft having a first end and a second end distal from the first end, the shaft also having a channel disposed from the first end of the shaft to the second end of the shaft and disposed to allow suction through the shaft;
   a nozzle integrally formed with the first end of the shaft, the nozzle being pliable;
   an inlet disposed through an exterior surface of the shaft and in operable communication with the channel, the inlet being disposed to be manually covered and uncovered by one or more fingers of a single hand to control suction through the shaft;
   a finger rest coupled to the shaft;
   a conduit that outputs received irrigation solution from the handpiece; and
   a dispenser coupled to the conduit and coupled to an irrigation source having the irrigation solution, wherein the dispenser is configured to be alternatively controlled to output, from the conduit to a location outside the handpiece, a first form of the irrigation solution and a first amount of volume of the irrigation solution during a first period of operation of the finger-controlled handpiece, and a second form of the irrigation solution and a second amount of volume of the irrigation solution during a second period of operation of the finger-controlled handpiece, wherein the first form and the first amount of volume are distinct from the second form and the second amount of volume, and wherein an amount of pressure applied manually to the irrigation source is associated with whether the first form or the second form is a spray, a stream or a droplet.

9. The handpiece of claim 8, wherein the nozzle is comprised of at least one of rubber or plastic.

10. The handpiece of claim 8, wherein the first end of the nozzle has a substantially flat configuration.

11. The handpiece of claim 8, wherein the nozzle and the shaft are integrally formed with one another via welding or adhesive.

12. A finger-controlled handpiece disposed to provide suction and irrigation of a body cavity, the handpiece comprising:

a shaft having a first end and a second end distal from the first end, the shaft also having a channel disposed from the first end of the shaft to the second end of the shaft and that allows suction through the shaft;

a nozzle coupled to the first end of the shaft;

an inlet having at least one portion disposed through a first position on an exterior surface of the shaft and in operable communication with the channel, the inlet being disposed to be manually covered and uncovered by one or more portions of a single hand to control suction through the shaft;

a finger rest coupled to a second position on the exterior surface of the shaft and located between the first end of the shaft and the second end of the shaft, the finger rest disposed to receive at least the one or more portions of the single hand or another portion of the single hand to facilitate stabilization of the handpiece;

a flap surrounding at least a portion of a boundary of the inlet; and a dispenser coupled to an irrigation source having the irrigation solution, wherein the dispenser is capable of outputting a spray or a droplet from, at least, the dispenser, wherein whether the irrigation solution output is a spray or a droplet is based on an amount of positive pressure applied to the irrigation solution in response to a respective amount of depression of an irrigation source coupled to the dispenser and that contains the irrigation solution, wherein a first type of depression of the irrigation source is associated with a first type of irrigation solution output and wherein a second type of depression of the irrigation source is associated with a second type of irrigation solution output.

* * * * *